(12) United States Patent
Guala

(10) Patent No.: US 9,352,086 B2
(45) Date of Patent: May 31, 2016

(54) ONE-WAY VALVE FOR MEDICAL LINES

(71) Applicant: Industrie Borla S.p.A., Moncalieri (Turin) (IT)

(72) Inventor: Gianni Guala, Turin (IT)

(73) Assignee: INDUSTRIE BORLA S.P.A., Moncalieri (Turin) (IT)

( * ) Notice: Subject to any disclaimer, the term of this patent is extended or adjusted under 35 U.S.C. 154(b) by 491 days.

(21) Appl. No.: 13/926,614

(22) Filed: Jun. 25, 2013

(65) Prior Publication Data

US 2014/0005612 A1 Jan. 2, 2014

(30) Foreign Application Priority Data

Jun. 27, 2012 (IT) .............................. TO2012A0575

(51) Int. Cl.
*A61M 5/168* (2006.01)
*A61M 5/165* (2006.01)
*A61M 39/24* (2006.01)

(52) U.S. Cl.
CPC ........... *A61M 5/16804* (2013.01); *A61M 5/165* (2013.01); *A61M 39/24* (2013.01); *A61M 2005/1657* (2013.01); *A61M 2039/246* (2013.01); *A61M 2205/75* (2013.01)

(58) Field of Classification Search
CPC .......... A61M 39/24; A61M 2039/242; A61M 2039/2433
See application file for complete search history.

(56) References Cited

U.S. PATENT DOCUMENTS

| | | | |
|---|---|---|---|
| 3,970,490 A | 7/1976 | Raines et al. | |
| 4,450,078 A | 5/1984 | Walker et al. | |
| 5,195,986 A | 3/1993 | Kamen | |
| 6,086,762 A | 7/2000 | Guala | |
| 6,409,707 B1 * | 6/2002 | Guala | ................... A61M 39/24 137/843 |
| 2012/0004623 A1 * | 1/2012 | Tumminaro | .......... A61M 39/24 604/247 |

FOREIGN PATENT DOCUMENTS

| | | |
|---|---|---|
| EP | 0887085 A2 | 12/1998 |
| EP | 1093828 B1 | 3/2003 |
| EP | 1099457 B1 | 9/2003 |
| EP | 1946793 A1 | 7/2008 |
| WO | 2010107597 A1 | 9/2010 |

OTHER PUBLICATIONS

Italian Search Report dated Apr. 26, 2013, for corresponding Italian Patent Application No. TO2010A0000575.
European Search Report for corresponding Italian Application No. 13170589.9-1662, completed on Oct. 29, 2013, and mailed on Nov. 6, 2014.

* cited by examiner

*Primary Examiner* — Laura Bouchelle
(74) *Attorney, Agent, or Firm* — Heslin Rothenberg Farley & Mesiti P.C.; Victor A. Cardona, Esq.

(57) ABSTRACT

A one-way valve for medical infusion lines includes a first tubular connector and a second tubular connector, which define, respectively, an upstream passage and a downstream passage, which are coaxial and set transversely between which is a diaphragm made of elastically deformable material co-operating in a fluid-tight way with an annular seat to keep the valve normally closed. A filter, integrated in the valve, is axially clamped and blocked between the first tubular connector and the diaphragm.

18 Claims, 5 Drawing Sheets

ONE-WAY VALVE FOR MEDICAL LINES

CROSS REFERENCE TO RELATED APPLICATIONS

This application claims priority from Italian Patent Application No. TO2012A000575 filed on Jun. 27, 2012, the entire disclosure of which is incorporated herein by reference.

FIELD OF THE INVENTION

The present invention relates to one-way valves for medical lines, for example, infusion lines and the like, of the type comprising a body formed by a first tubular connector and a second tubular connector that define, respectively, an upstream passage and a downstream passage, which are coaxial and set transversely between which is a diaphragm made of elastically deformable material, which co-operates in a fluid-tight way with an annular valve seat to keep the one-way valve normally closed. A predetermined pressure of fluid in the upstream passage brings about a displacement or an elastic deformation of the diaphragm and consequent opening of the valve, i.e., opening of the communication between the upstream passage and the downstream passage.

Valves of this sort are used, for example, as check valves, which are purposely designed to open when the pressure in the upstream passage exceeds a predetermined relatively modest threshold value, and then to reclose promptly so as to prevent, with the maximum degree of safety, any reflux from the downstream passage to the upstream passage when the pressure in the latter drops again below the threshold value, or else in the case of an even minimal overpressure within the downstream passage.

PRIOR ART

From the patent documents Nos. EP-1099457B1, EP-1093828B1 and 1946793A1, all of which are filed in the name of the present applicant, there are known one-way valves of the type specified above, in which the annular valve seat is defined by a wall with conical surface of the first tubular connector, diverging towards the second tubular connector, and the diaphragm is constituted by the bottom wall of a cup-shaped element, the outer peripheral edge of which is normally pressed in fluid-tight contact against the annular valve seat under an axial thrust exerted by the side wall of the cup-shaped element. In operation, when the pressure within the upstream passage reaches the aforesaid predetermined value, an axial displacement of the bottom wall of the cup-shaped element is produced in the direction of the second tubular connector, as a result of which the corresponding outer peripheral edge contracts radially, moving away from the annular valve seat with a high degree of promptness and immediacy of opening of the one-way valve.

In applications on medical infusion lines, a filter is normally provided for filtering any possible impurities contained in the fluid that traverses the valve. Traditionally, the filter consists of an element separate from the valve, set along the line upstream of the first tubular connector, or else a filtering body inserted within the upstream passage defined by the aforesaid first tubular connector.

Both of the solutions prove far from practical and to some extent complicate production of the medical line.

From the document No. WO-2010/107597, a one-way valve is known of the type specified above, in which the filter is integrated within the body and consists of a permeable membrane set transversely and carried by a peripheral ring engaged with interference fit or snap-action fit on an internal annular flange of the body set upstream of the valve seat with respect to the direction of flow through the valve.

The above fit does not ensure the necessary stability of retention of the filter, which can be easily disengaged from the flange of the body, with the consequent risk of opening paths of flow without any filtering.

SUMMARY OF THE INVENTION

The object of the present invention is to overcome the above drawback, and this object is achieved thanks to the fact that the one-way valve is of the type defined in the pre-characterizing part of claim 1, the peculiar characteristic of which lies in the fact that the annular element of the filtering membrane is axially clamped and blocked between the first and second tubular connectors.

BRIEF DESCRIPTION OF THE DRAWINGS

The invention will now be described in detail with reference to the annexed drawings, which are provided purely by way of non-limiting example and in which.

DETAILED DESCRIPTION OF THE INVENTION

Figure 1:
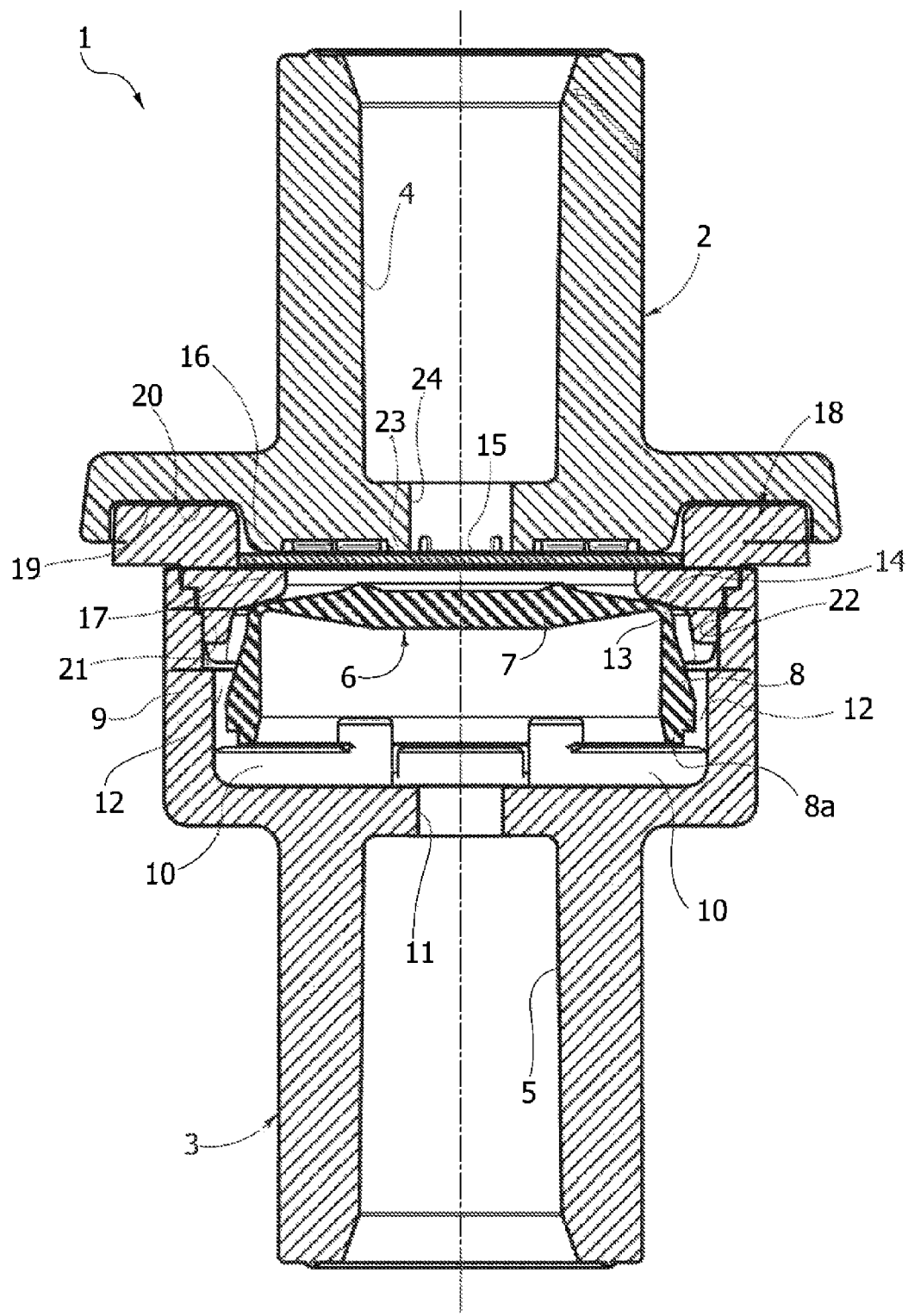
FIG. 1 is a schematic view in axial section of a one-way valve according to a first embodiment of the invention.
Figure 2:
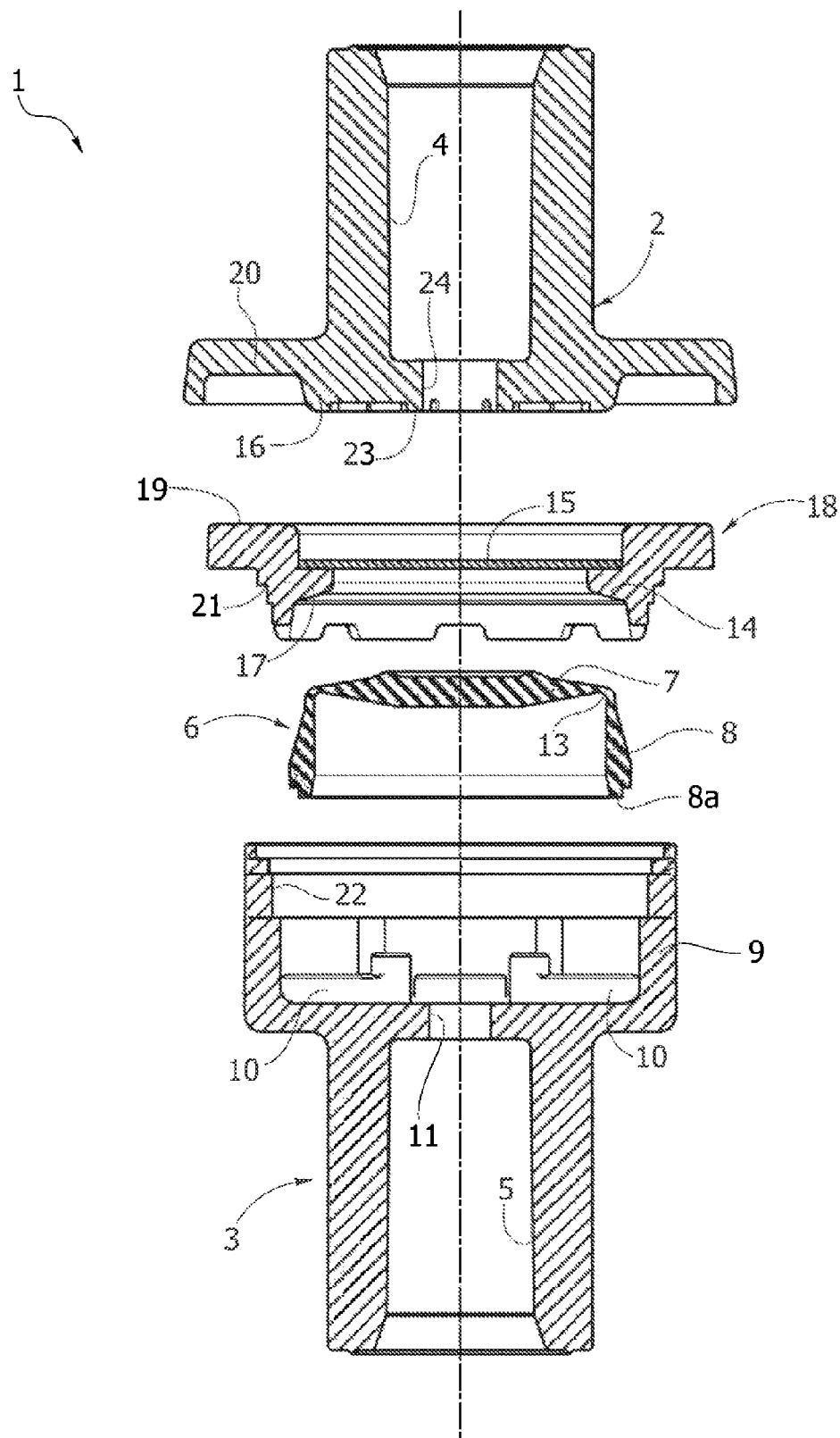
FIG. 2 is an exploded view of the valve of FIG. 1.

With initial reference to FIGS. 1 and 2, the reference number 1 designates as a whole the body of a tubular connector for tube-to-tube connection of a medical line for infusion, transfusion, and the like. It should be noted that the connector could be prearranged, in a way in itself known, for luer-to-tube, or else tube-to-luer, or luer-to-luer connections, or other types of connection normally used in medical lines.

The body of the connector 1 comprises, in a way generally in itself known, for example, from the already cited document No. EP-1946793A1, a first tubular connector 2 and a second tubular connector 3, both of which are normally made of a suitable moulded thermoplastic material, axially joined together in a permanent way, with the modalities clarified in what follows.

The first and second tubular connectors 2, 3 define, respectively, an upstream passage or inlet passage 4 and a downstream passage or outlet passage 5 which can be connected to respective sections of tubing of the medical line.

Set between the upstream passage 4 and the downstream passage 5 is a one-way valve, the open/close element of which, set within a widened portion 9 of the tubular connector 3 coaxially with the latter, consists of a cup-shaped element 6, which comprises a circular bottom wall 7 and a skirt or side wall 8 and is conveniently made of a single piece of soft elastomeric material, for example, silicone rubber.

The free edge 8a of the skirt 8 rests on a radial array of transverse projections 10 formed at the base of the widened portion 9 and delimiting respective radial channels that communicate on one side with a restricted central passage 11, which is in turn in communication with the downstream passage 5, and on the other with peripheral axial passages 12 designed to be set in communication, in the condition of opening of the open/close element 6, with the upstream passage 4. Preferably, the resting surface between the free edge 8a of the skirt 8 and the sectors 10 is provided, according to what is envisaged in the already cited document No. EP-1946793A1, only in angular portions separated by portions that do not provide a rest.

The edge of the open/close element 6 comprised between the bottom wall 7 and the skirt 8, which is designated by 13, constitutes the sealing element of the open/close element 6 which cooperates with an annular valve seat 14 with conical surface. In the condition of closing of the valve (represented in FIG. 1), the skirt 8 is subjected to a predetermined axial elastic preload and presses the edge 13 in fluid-tight contact against the valve seat 14 so as to interrupt communication between the axial passages 12, and hence the downstream passage 5, and the upstream passage 4. When an overpressure of higher degree than a pre-set threshold value is produced within the upstream passage 4, the axial displacement of the bottom wall 7 of the open/close element 6 in the direction of the tubular connector 3 causes separation between the edge 13 and the valve seat 14, setting the upstream passage 4 in communication with the downstream passage 5.

According to the peculiar characteristic of the invention, the connector 1 incorporates, in an integrated way, a filter set through the line of flow between the upstream passage 4 and the downstream passage 5, which is axially blocked between the first tubular connector 2 and the second tubular connector 3, upstream of the open/close element 6 of the valve with respect to the flow through the body 1 of the valve.

In the embodiment represented in FIGS. 1 and 2 the filter consists of a transverse membrane 15, made of an appropriate permeable filtering material, the outer peripheral edge of which is fixed on a radially inner flange 17 of an annular element 18 set between the tubular connectors 2 and 3. The surface of the flange 17 opposite to the filtering membrane 15 defines the annular valve seat 14.

On the side opposite to the flange 17 the membrane 15 frontally bears upon an annular projection 16 of the tubular connector 2, projecting axially towards the tubular connector 3. The annular element 18 has a peripheral flange 19 for front coupling to a radially outer flange 20 of the tubular connector 2, and a stepped side wall 21 for coupling to a complementary stepped internal surface 22 of the widened portion 2 of the tubular connector 3. Fixing between the flanges 19 and 20 on one side and the stepped walls 21 and 22 on the other can be obtained by ultrasound welding, gluing, or any other suitable system.

The central part of the membrane filter 15 moreover rests against an inner axial annular projection 23 of the tubular connector 2 and faces a restricted terminal portion 24 of the inlet passage 4.

Figure 3:
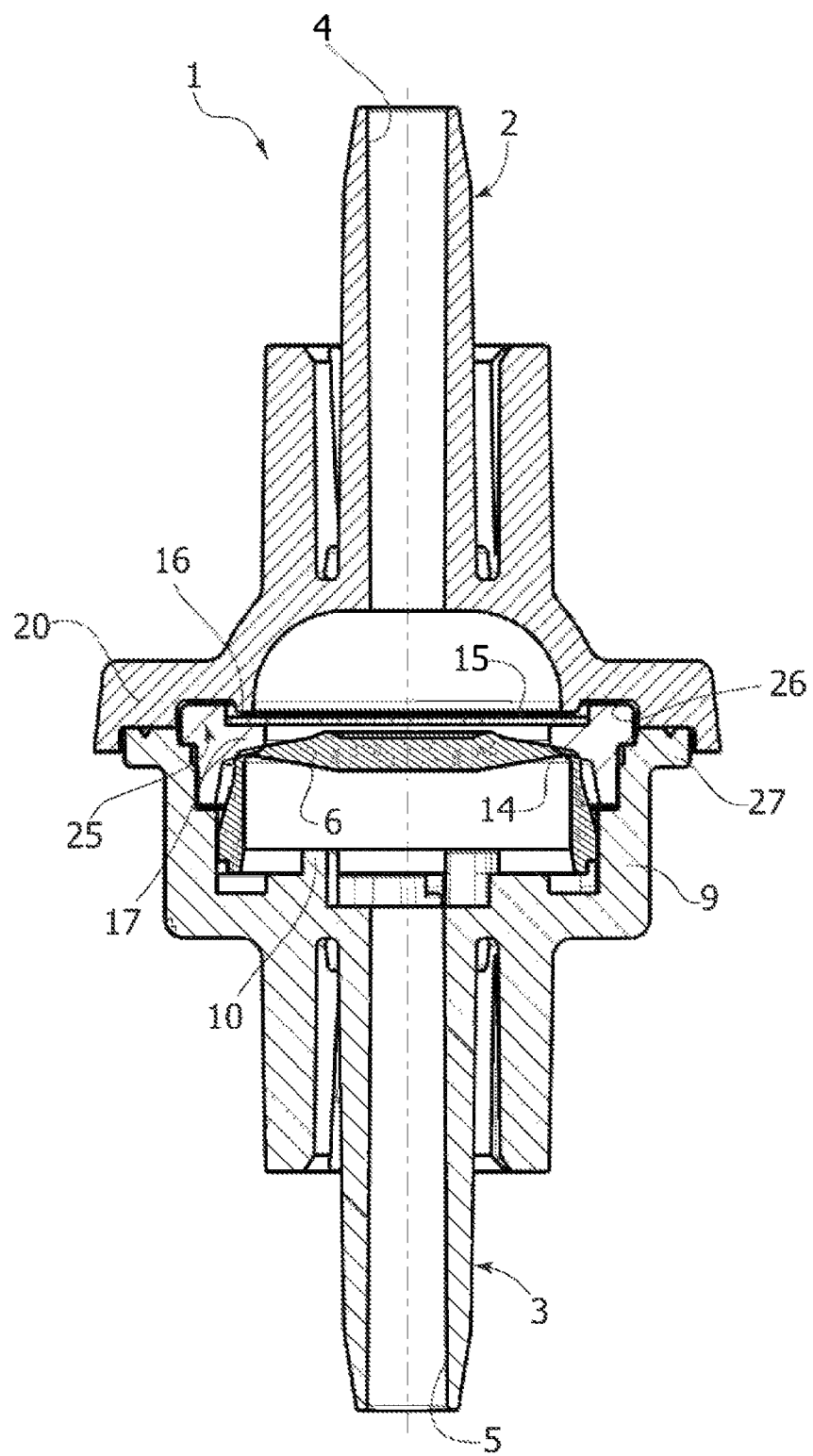
FIG. 3 is a view similar to that of FIG. 1 which shows a second embodiment of the invention.

The variant of the valve connector according to the invention illustrated in FIG. 3, is generally similar to the embodiment described previously, and here only the differences will be described in detail, using the same reference numbers for parts that are identical or similar.

In the above variant, the annular element of the filtering membrane 15, designated by 25, is axially blocked in an annular seat 26 formed between the annular flange 20 of the tubular connector 2 and a complementary annular flange 27 of the tubular connector 3, which in this case are directly fixed to one another. The annular element 25 is conveniently welded inside the flange 27, which is in turn welded to the flange 20.

The filtering membrane 15 is, also in this case, inserted peripherally between the flange 17 of the annular element 25 and the annular projection 16 of the tubular connector 2 and the valve seat 14 for the open/close element 6 is also formed by the surface of the flange 17 of the annular element 25 opposite to the one on which the peripheral edge of the membrane 15 is fixed.

Figure 4:
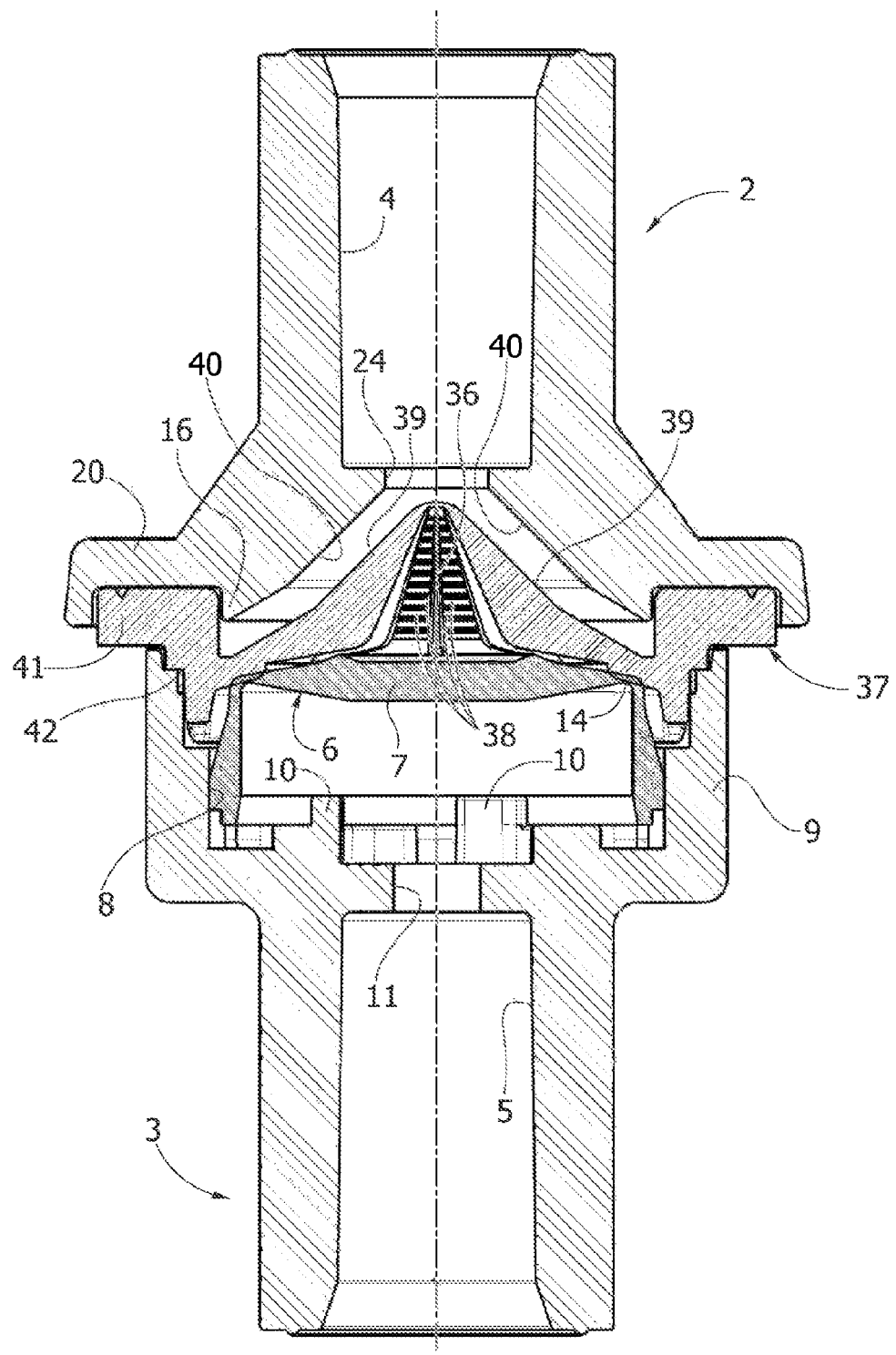
FIG. 4 is a view similar to that of FIG. 1 which shows a third embodiment of the invention.
Figure 5:
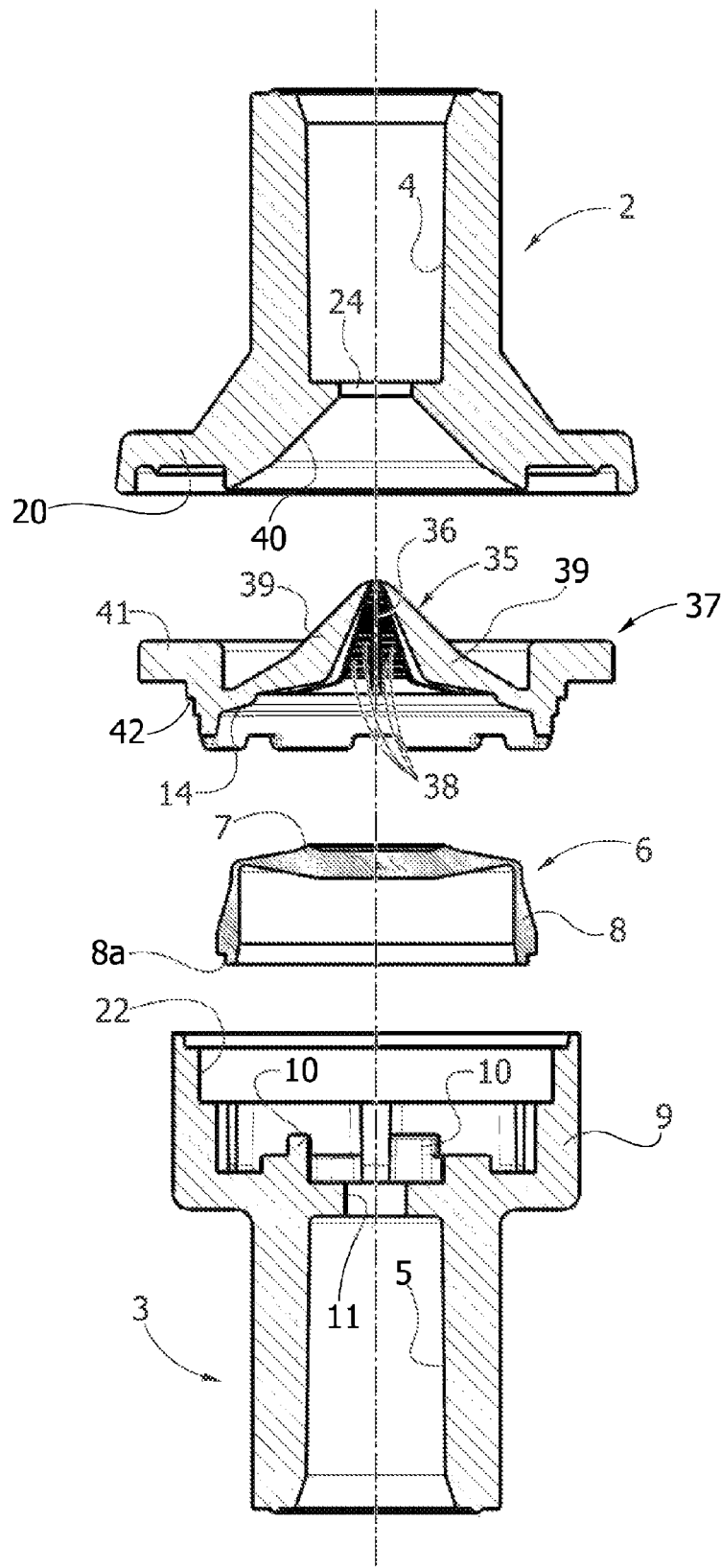
FIG. 5 is an exploded view of the valve of FIG. 4.

In the variant represented in FIGS. 4 and 5, where likewise the same reference numbers are used to designate parts that are identical or similar to the ones already described with reference to the previous embodiments, the filter is formed by a body made of moulded plastic material 35 having a perforated wall 36 and made of a single piece with an intermediate annular element 37 axially blocked between the radially outer annular flange 20 of the first tubular connector 2 and the second tubular connector 3.

The perforated wall 36 is formed with a series of microslits 38 separated by intermediate septa 39. Alternatively, the aforesaid perforated wall 36 could present a micro-grid conformation.

In the case of the example illustrated, the perforated wall 36 has a generally conical shape converging towards the inlet passage 4 and faces a wall 40 having a complementary conical shape of the first tubular connector 2. Its apex projects towards the restricted terminal portion 24 of the inlet passage 4.

Also in this case, the intermediate annular element 37 forms the annular valve seat 14 for the diaphragm 6 and has a peripheral flange 41 for front coupling with the radially outer annular flange 20 of the first tubular connector 2. Its side wall is also formed with steps 42 for coupling to the stepped internal surface 22 of the second tubular connector 3.

It should be noted that the perforated wall 36 of the filter body 35 could present a surface geometrically different from the one illustrated; for example, it could be spherical.

Of course, details of construction and the embodiments may vary widely with respect to what has been described and illustrated herein, without thereby departing from the scope of the present invention as defined in the ensuing claims.

The invention claimed is:

1. A one-way valve for medical infusion lines, comprising:
    a body having a first tubular connector and a second tubular connector, which define, respectively, an upstream passage and a downstream passage coaxial with each other;
    a diaphragm set transversely between said upstream passage and said downstream passage, said diaphragm made of elastically deformable material co-operating in a fluid-tight way with an annular valve seat to keep said valve normally closed;
    wherein a predetermined pressure of fluid in said upstream passage brings about a displacement or an elastic deformation of said diaphragm and consequent opening of said valve;
    said valve being provided with a filter integrated within the body and including a permeable membrane carried by an annular element and set between said first tubular connector and said diaphragm;
    said annular element is axially clamped and blocked between said first and second tubular connectors; and
    wherein said annular element is axially blocked between a radially outer annular flange of said first tubular connector and said second tubular connector.

2. The valve according to claim 1, wherein said membrane is peripherally clamped between a radially inner annular projection of said first tubular connector and a radially inner flange of said annular element.

3. The valve according to claim 2, wherein said annular element is formed with said annular valve seat.

4. The valve according to claim 3, wherein said annular element has a peripheral flange for front coupling with said radially outer annular flange of said first tubular connector, and a stepped side wall for fixing to a complementary stepped internal surface of said second tubular connector.

5. The valve according to claim 3, wherein said annular element is blocked within an annular seat formed between a radially outer annular flange of said first tubular connector and a complementary annular flange of said second tubular connector, which are directly fixed to one another.

6. The valve according to claim 2, wherein said annular element has a peripheral flange for front coupling with said radially outer annular flange of said first tubular connector, and a stepped side wall for fixing to a complementary stepped internal surface of said second tubular connector.

7. The valve according to claim 2, wherein said annular element is blocked within an annular seat formed between a radially outer annular flange of said first tubular connector and a complementary annular flange of said second tubular connector, which are directly fixed to one another.

8. The valve according to claim 1, wherein said annular element is blocked within an annular seat formed between a radially outer annular flange of said first tubular connector and a complementary annular flange of said second tubular connector, which are directly fixed to one another.

9. The valve according to claim 1, wherein said filter is formed by a body made of moulded plastic material having a perforated wall and made of a single piece with an intermediate annular element axially blocked between a radially outer annular flange of said first tubular connector and the second tubular connector.

10. The valve according to claim 9, wherein said perforated wall is formed with a series of micro-slits separated by intermediate septa.

11. The valve according to claim 10, wherein said perforated wall has a generally conical shape converging towards said inlet passage.

12. The valve according to claim 9, wherein said perforated wall has a generally conical shape converging towards said inlet passage.

13. The valve according to claim 12, wherein said perforated wall faces a wall having a complementary conical shape of said first tubular connector and projects towards a restricted terminal portion of said inlet passage.

14. The valve according to claim 9, wherein said intermediate annular element forms said annular valve seat.

15. The valve according to claim 14, wherein said intermediate annular element has a peripheral flange for front coupling with a radially outer annular flange of said first tubular connector, and a stepped side wall for coupling to a complementary stepped internal surface of said second tubular connector.

16. The valve according to claim 9, wherein said intermediate annular element has a peripheral flange for front coupling with a radially outer annular flange of said first tubular connector, and a stepped side wall for coupling to a complementary stepped internal surface of said second tubular connector.

17. The valve according to claim 1, wherein said diaphragm comprises a bottom wall of a cup-shaped element, an outer peripheral edge of which is normally pressed in fluid-tight contact against said annular valve seat under the action of an axial thrust exerted by a side wall of said cup-shaped element.

18. The valve according to claim 17, wherein the side wall of said cup-shaped element has a free edge set resting against a grooved transverse surface of said second tubular connector defined by a plurality of radial projections (10) angularly separated by angular portions that do not provide a rest.

\* \* \* \* \*